United States Patent
Heinrich et al.

(10) Patent No.: US 6,881,408 B1
(45) Date of Patent: Apr. 19, 2005

(54) IMMUNOADSORBER FOR USE IN SEPSIS THERAPY

(75) Inventors: Hans-Werner Heinrich, Riemserort (DE); Hans-Jürgen Hahn, Karlsburg (DE); Udo Meyer, Hastorf (DE); Peter Kruschke, Greifswald (DE); Heinz-Jürgen Wagner, Berlin (DE)

(73) Assignee: Bioserv AG, Rostock (DE)

( * ) Notice: Subject to any disclaimer, the term of this patent is extended or adjusted under 35 U.S.C. 154(b) by 0 days.

(21) Appl. No.: 09/937,126

(22) PCT Filed: Mar. 23, 2000

(86) PCT No.: PCT/DE00/00927

§ 371 (c)(1),
(2), (4) Date: Dec. 19, 2001

(87) PCT Pub. No.: WO00/58005

PCT Pub. Date: Oct. 5, 2000

(30) Foreign Application Priority Data

Mar. 26, 1999 (DE) .......................... 199 13 707

(51) Int. Cl.⁷ .............................................. A61K 39/395
(52) U.S. Cl. ................ 424/140.1; 424/139.1; 604/5.01; 604/5.02; 604/5.04
(58) Field of Search .......................... 424/140.1, 139.1; 604/5.01, 5.02, 5.04

(56) References Cited

U.S. PATENT DOCUMENTS

| 5,626,843 A | * | 5/1997 | Surkovich et al. ....... 424/140.1 |
| 5,853,722 A | | 12/1998 | Rollins et al. ........... 424/145.1 |
| 6,074,642 A | * | 6/2000 | Wang et al. ............. 424/145.1 |
| 6,193,681 B1 | * | 2/2001 | Davidner et al. ......... 604/6.08 |
| 6,287,516 B1 | * | 9/2001 | Matson et al. ............... 422/44 |

FOREIGN PATENT DOCUMENTS

WO    WO 98/34959    8/1998

* cited by examiner

*Primary Examiner*—David Saunders
(74) *Attorney, Agent, or Firm*—Norris McLaughlin & Marcus PA

(57) ABSTRACT

The invention relates to immunoadsorbers for use in sepsis therapy, in particular for removal of complement factors and lipopolysaccharides (LPS) and, if need be, further sepsis mediators such as TNF and interleukins from body fluids, methods for their production and their use.

17 Claims, No Drawings

SEQUENCE LISTING

<160> NUMBER OF SEQ ID NOS: 20

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: designed
      synthetical peptide  of the complement factor  C3a

<400> SEQUENCE: 1

Lys Cys Cys Glu Asp Gly Met Arg Gln Asn Pro Met Arg
 1               5                  10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: designed
      synthetical peptide    of the   complement factor C3a

<400> SEQUENCE: 2

Arg Phe Ser Cys Gln Arg Arg Thr Arg Phe Ile Ser Leu
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: designed
      synthetical peptide of the complement factor C3a

<400> SEQUENCE: 3

Ile Thr Glu Leu Arg Arg Gln His Ala Arg Ala Ser
 1               5                  10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: designed
      synthetical peptide of the complement factor C5a

<400> SEQUENCE: 4

Gln Ala Asp Tyr Lys Asp Asp Asp Lys Leu Pro Ala Glu
 1               5                  10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: designed
      synthetical peptide  of complement factor C5a

```
<400> SEQUENCE: 5

Asp Asp Lys Leu Pro Ala Glu Gly Leu Asp Ile Glu Asn Ser
 1               5                  10

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: designed
      synthetical peptide of the interleukin 1 alpha

<400> SEQUENCE: 6

Asn Cys Tyr Ser Glu Asn Glu Asp Ser Ser Ser Ile Asp
 1               5                  10

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: designed
      synthetical peptide  of the interleukin 1alpha

<400> SEQUENCE: 7

Gly Ala Tyr Lys Ser Ser Lys Asp Asp Ala Lys Ile Thr
 1               5                  10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: designed
      synthetical peptide of the inerleukin 1 alpha

<400> SEQUENCE: 8

Trp Glu Thr His Gly Thr Lys Asn Tyr Phe Thr Ser
 1               5                  10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: designed
      synthetical peptide  of the interleukin 1beta

<400> SEQUENCE: 9

Arg Ile Ser Asp His His Tyr Ser Lys Gly Phe Arg Gln Ala
 1               5                  10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: designed
      synthetical peptide  of interleukin 1beta

<400> SEQUENCE: 10

Val Gln Gly Glu Glu Ser Asn Asp Lys Ile Pro Val Ala
 1               5                  10

<210> SEQ ID NO 11
<211> LENGTH: 17
<212> TYPE: PRT
```

```
<213> ORGANISM: Artificial Sequence
<220> FEATURE:
<223> OTHER INFORMATION: Description of Artificial Sequence: designed
      synthetical peptide   of interleukin 1beta

<400> SEQUENCE: 11

Glu Ser Val Asp Pro Lys Asn Tyr Pro Lys Lys Met Glu Lys Arg
 1               5                  10                  15

Phe

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: designed
      synthetical peptide of interleukin 6

<400> SEQUENCE: 12

Ala Pro His Arg Gln Pro Leu Thr Ser Ser Glu Arg Ile Asp Lys Gln
 1               5                  10                  15

Ile

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: designed
      synthetical peptide   of interleukin 6

<400> SEQUENCE: 13

Gln Asn Arg Phe Glu Ser Ser Glu Glu Gln Ala Arg Ala
 1               5                  10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: designed
      synthetical peptide   of interleukin 6

<400> SEQUENCE: 14

Ala Ile Thr Thr Pro Asp Pro Thr Thr Asn Ala Ser
 1               5                  10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: designed
      synthetical peptide   of interleukin 10

<400> SEQUENCE: 15

Ser Pro Gly Gln Gly Thr Gln Ser Glu Asn Ser Cys Thr
 1               5                  10

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: designed
      synthetical peptide of interleukin 10
```

```
-continued

<400> SEQUENCE: 16

Gln Met Lys Asp Gln Leu Asp Asn Leu Leu Leu Lys Glu Ser
  1               5                  10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: designed
      synthetical peptide   of interleukin 10

<400> SEQUENCE: 17

Met Pro Gln Ala Glu Asn Gln Asp Pro Asp Ile Lys Ala
  1               5                  10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: designed
      synthetical peptide     of interleukin 10

<400> SEQUENCE: 18

Leu Pro Cys Glu Asn Lys Ser Lys Ala Val Glu Gln
  1               5                  10

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: designed
      synthetical peptide   of TNF alpha

<400> SEQUENCE: 19

Val Arg Ser Ser Ser Arg Thr Pro Ser Asp Lys Pro Val Ala
  1               5                  10

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: designed
      synthetical peptide   of TNF alpha

<400> SEQUENCE: 20

Lys Ser Pro Cys Gln Arg Glu Thr Pro Glu Gly Ala Glu Ala Lys Pro
  1               5                  10                  15

Trp
```

IMMUNOADSORBER FOR USE IN SEPSIS THERAPY

The invention in question relates to an immunoadsorber for use in sepsis therapy, in particular for removing complement factors and lipopolysaccharides (LPS) as well as, if need be, TNF and interleukins from body fluids and methods for their production and their use.

Every year, about 3.5 million patients suffer from sepsis in the USA, Japan and the EU. With a total number of inhabitants of 785 million, the incidence for these countries is less than 0.5%. But when hospitalised patients are examined with regard to the frequency of suffering, 2.0±0.16 cases of sepsis are found per 100 hospital admissions. The enormous health political and individual importance can also be seen from the observation that about 25% of these patients also suffer the syndrome of a septic shock, characterised by the lethality rate of >45%, even with most intensive medicinal care by highly qualified specialists in institutions with modern equipment (intensive care units).

The risk of suffering a septic shock is very high especially with poly-traumatised patients (traffic accidents, burns, serious operations). Alongside infection from the outside, breaking through the intestinal barrier for gram-negative bacteria normally occurring in the intestines as a result of a partial loss of function of the immune system of these patients and thus an infection "from the inside" can be detected.

In more than 50% of the cases, gram-negative bacterial or their cell-wall components, endotoxins (lipopolysaccharides, LPS), cause the septic shock. The LPS released by bacterial binds to a serum protein (LBP) and is then absorbed by the LPS receptors of the monocytes/macrophages (CD14). The CD14+ cells activated in this way produce cytokines (TNFα, Interleukin-1' (IL-1), IL-6, IL-8), which have their effect via cytokine receptors of the target cells.

Parallel to the stimulation of the monocytes and macrophages, the complement system is activated. It is an integrated part of the immunological defence of mammals for direct and unspecific combating of bacterial micro-organisms and foreign particles. Of the complement proteins occurring in the blood serum, primarily proenzymes activated by proteolytic fission, the C3 protein with a serum concentration of about 1 g/l plays a central role. After contact of the micro-organisms with the C3, the complement protein C3a is split off and, on the one hand, the formation of C5 convertase is initiated by the resultant C3b (alternative way of complement activation) and, on the other hand, the reaction is amplified by the C3B converting to C3 convertase due to depositing of serum factors. The complement protein C5 also occurring in serum is now proteolytically fissured by the C5 convertase, which is provided in larger amounts, also forming C5a. Further complement proteins (C6–C9) deposit on the resulting C5b until finally the polymeric hydrophobic membrane attack complex (MAC) is formed, settling in the bacteria membrane (opsonidisation) and forming pores, which lead to phagocytosis and thus to the elimination of the micro-organisms (and the bound MAC). The complement factors C3a and C5A (anaphylatoxins) released in the process of the complement activation result in stimulation of the phagocytising cells to the location of the bacterial attack by increasing the vascular permeability and the release of chemotoxins induced thereby. The reduction of the number of bacteria results in a reduction of the activation of the complement system. This direct and unspecific reaction is closely connected with the other immunological defence systems insofar as the synthesis and release of the cytokines essential for cellular defence is regulated, for example by complement factors. In order to bring about the inflammatory effect, C3a and C5a are bound to specific cell-based receptors, which for their part are expressed in different strengths as a function of the immune reactivity. In order to keep the immune defence permanently ready for activity, activated complement factors are detectable not only after an attack with micro-organisms, but also an integrated part of the serum of standard persons with a concentration of 1–10 ng/ml.

The plasma levels of the anaphylatoxins can be increased by a factor of more than one thousand, particularly in a developed sepsis, acute pulmonary failure and in moribund patients.

Almost exclusively on the basis of in vitro examinations, there exist various, mainly unspecifically effective variations of solutions in order to eliminate the effects of various complement factors, which however can hardly be tested under in vivo conditions on account of the side effects to be expected (e.g. WO-A-98/34959).

In ex vivo methods for the prevention of complement activation by artificial, extracorporal surfaces (e.g. surface coatings), an unspecific complement activation was successfully carried out. Further, selective removal of activated complement factors making use of specific C5 antibodies is known from U.S. Pat. No. 5,853,722 and certainly also to be preferred, especially as highly affined antibodies have been generated in the meantime against all the components of the complement system.

The functional cascade manifested is primarily used to eliminate the bacteria penetrating into the organism. But as soon as a discrepancy occurs between the number and/or virulence of the penetrating bacteria and the elimination capacity of the immune system (e.g. in post-traumatic immune deficiency), an excessive activation is observed, subsequently accompanied by a massive release of "shock mediators" (interleukins, thrombocyte activation factor (PAF), but also oxygen radicals, prostagiandins and their metabolic products), thus further limiting the elimination capacity for LPS. In addition, CD14-negative cells (e.g. endothellae) are also activated by the LPS, as soluble CD14 (sCD14) exists in the blood plasma as an LPS trapper, facilitating binding to these cells and inducing the formation and release of further shock mediators, thus reinforcing the circulus vitiosus. As the shock mediators act selectively, but not specifically, function restrictions in various cells and organs are observed (blood coagulation system, circulation, complement system), with the result that the inflammation reactions attacking the entire organisms initiate shock genesis, leading to irreversible organ damage, to circulation collapse and death.

In order to break through this chain of functions, various therapy strategies have been studies.

Interruption of the cascade with antibodies interrupting the LPS binding to proteins (LBP, sCD14), to the receptor (CD14), to released cytokines or to cytokine receptors or with antagonists blocking the functional areas of the receptors did achieve impressive success in various sepsis models in animal experiments, but there are still no clinically tested, successful prevention and/or therapy studies.

It was not possible to fulfil the high expectations, as it was increasingly seen that LPS also influences and changes the functional condition of cells and tissue which are not impaired by these therapeutic approaches. In addition, it must be taken into account that an LPS (immune complex) inactivated by an antibody/antagonist must be eliminated in order to exclude a biological reactivity on a permanent basis. But the elimination is also a function of the immune system, which, as it is greatly weakened, can hardly or only very imcompletely fulfil this task.

The development of the septic shock is a very dynamic occurrence of primarily varying genesis, in which various mediators cause highly differing reactions within a short period of time, these quickly leading to the expression of the septic shock by dysregulation after an initial life-maintaining function.

Therefore, the invention was based on the task of developing an immunoadsorption system of modular construction, in particular for extra-corporal detoxification, enabling a reduction of the plasma and tissue levels specific to the patient.

Inter alia, the invention is based on the knowledge that TNFα has a key role to play in this regulation system. It is released inter alia by macrophages as a result of various "external" influences such as injuries, inflammations, infections, septicaemia and induces a local and systemic activation of the unspecific and specific defence system via a cytokine cascade (IL-1, IL-6). Clinically, a massive TNFα release is expressed by increased body temperature, lack of appetite and all the subsequent symptoms of a catabolic metabolism situation. In pathogenesis of the sepsis, activation of the macrophages and thus the release of TNFα appears to be of essential importance for a survival of the patient in the early phase of this disease, whereas the continued state of activation results in the de-compensation of all defence reactions in the further course.

The task of the invention was solved by an immunoadsorber for use in sepsis therapy. The immunoadsorber according to the invention is particularly used for the removal of complement factors and lipopolysaccharides (LPS) as well as the removal of further sepsis mediators, and also TNF and interleukins from body fluids, if need be. It is characterised by carrier materials of organic or synthetic polymers, to which both poly or monoclonal antibodies aimed against the complement factors C3a and/or C5a, and also antibodies aimed against lipopolysaccharides (LPS) are bound. In a preferred embodiment, antibodies aimed against further sepsis mediators are also bound to the carrier.

Preferably, these are polyclonal antibodies, particularly preferably avian antibodies of type IgY. The antibodies against sepsis mediators are contained according to the state of the dysregulation.

According to this invention, these are antibodies aimed against TNF, IL1, IL6, IL8 and/or IL 10.

Preferred antibodies against the complement factor C3a manifest specific activity against at least one of the following peptide sequences:
$NH_2$-KCCEDGMRQNPMR-COOH (SEQ ID NO: 1)
$NH_2$-RFSCQRRTRFISL-COOH (SEQ ID NO: 2)
$NH_2$-ITELRRQHARAS-COOH (SEQ ID NO: 3)

Preferred antibodies against the complement factor C5a possess specific activity against at least one of the following peptide sequences:
$NH_2$-QADYKDDDDKLPAE-COOH (SEQ ID NO: 4)
$NH_2$-DDKLPAEGLDIENS-COOH (SEQ ID NO: 5)

Preferred antibodies against IL1 α/β possess specific activity against at least one of the following peptide sequences:
$NH_2$-NCYSENEEDSSSID-COOH (SEQ ID NO: 6)
NH2 GAYKSSKDDAKIT-COOH (SEQ ID NO: 7)
$NH_2$-WETHGTKNYFTS-COOH (SEQ ID NO: 8)
$NH_2$-RISDHHYSKGFRQA-COOH (SEQ ID NO: 9)
$NH_2$-VQGEESNDKIPVA-COOH (SEQ ID NO: 10)
$NH_2$-ESVDPKNYPKKKMEKRF-COOH (SEQ ID NO: 11)

Preferred antibodies against IL6 possess specific activity against at least one of the following peptide sequences:
$NH_2$-APHRQPLTSSERIDKQI-COOH (SEQ ID NO: 12)
$NH_2$-QNRFESSEEQARA-COOH (SEQ ID NO: 13)
$NH_2$-AITTPDPTTNAS-COOH (SEQ ID NO: 14)

Preferred antibodies against IL10 possess specific activity against at least one of the following peptide sequences:
$NH_2$-SPGQGTQSENSCT-COOH (SEQ ID NO: 15)
$NH_2$-QMKDQLDNLLLKES-COOH (SEQ ID NO: 16)
$NH_2$-MPQAENQDPDIKA-COOH (SEQ ID NO: 17)
$NH_2$-LPCENKSKAVEQ-COOH (SEQ ID NO: 18)

Preferred antibodies against TNFα possess specific activity against at least one of the following peptide sequences:
$NH_2$-VRSSSRTPSDKPVA-COOH (SEQ ID NO: 19)
$NH_2$-KSPCQRETPEGAEAKPW-COOH (SEQ ID NO: 20)

The immunoadsorber according to the invention manifests membranes or particles customary per se of organic or synthetic polymers as carrier materials, e.g. of polystyrenes, carbohydrates such as cellulose or agarose derivatives, or of acrylates, with the specific antibodies being covalently linked to them or fixed to them via spacers or linkers.

The production of the immunoadsorbers according to the invention is done by methods known per se in that the antibodies aimed against C3a and/or C5a and LPS and, if need be, against further sepsis mediators are coupled covalently or adsorptively to the carrier materials or organic or synthetic polymers.

The specific antibodies are produced by immunisation known per se, preferably of small mammals such as mice, rats or rabbits, or birds, such as chickens, with the corresponding antigens.

The object of the invention is also the use of the immunoadsorbers in appliances for the removal of complement factors, LPS and, if need be, further mediators from body fluids such as blood plasma as a function of the patient-specific situation.

Preferably, the immunoadsorbers are used in sepsis therapy for piasmapherese in patients with sepsis or septic shock.

Although antibodies are available for most substances and are coupled to the various carriers by known methods, avian antibodies are preferably used, as they do not activate the complement system, unlike mammal antibodies. As the activating properties are bound to the $F_c$ part of the mammal antibodies, the $F_{ab}$ fragment fissured with papain can principally also be used.

According to the current state of knowledge, immobilised avian antibodies have no kind of unspecific effects on the human defence system. Birds, preferably chickens, are immunised with customary methods with or without the use of adjuvants. The specific immunoglobulins are excreted in the egg yolk and can be isolated from it with customary methods. They are covalently bound to micro-particles or membranes via the Fc part with known methods.

With the immunoadsorption system for extra-corporal detoxification according to the invention, there exists for the first time a selective system which can be used patient-specifically and by which dysregulations of the immune system can be rectified.

The invention is explained in more detail by the following examples:

EXAMPLE 1

Production of polyclonal antibodies by means of immunogenic peptides:

TABLE I

The peptides listed in Table I are produced by means of a solid phase synthesis

| Peptide sequence | | Antigen |
|---|---|---|
| KCCEDGMRQNPMR | (SEQ ID NO: 1) | C3a |
| RFSCQRRTRFISL | (SEQ ID NO: 2) | |
| ITELRRQHARAS | (SEQ ID NO: 3) | |
| QADYKDDDDKLPAE | (SEQ ID NO: 4) | C5a |
| DDKLPAEGLDIENS | (SEQ ID NO: 5) | |
| SPGQGTQSENSCT | (SEQ ID NO: 15) | IL10 |
| QMKDQLDNLLLKES | (SEQ ID NO: 16) | |
| MPQAENQDPDIKA | (SEQ ID NO: 17) | |
| LPCENKSKAVEQ | (SEQ ID NO: 18) | |
| NCYSENEEDSSSID | (SEQ ID NO: 6) | IL1 α |
| GAYKSSKDDAKIT | (SEQ ID NO: 7) | |
| WETHGTKNYFTS | (SEQ ID NO: 8) | |
| RISDHHYSKGFRQA | (SEQ ID NO: 9) | IL1 β |
| VQGEESNDKIPVA | (SEQ ID NO: 10) | |
| ESVDPKNYPKKKMEKRF | (SEQ ID NO: 11) | |
| APHRQPLTSSERIDKQI | (SEQ ID NO: 12) | IL6 |
| QNRFESSEEQARA | (SEQ ID NO: 13) | |
| AITTPDPTTNAS | (SEQ ID NO: 14) | |
| VRSSSRTPSDKPVA | (SEQ ID NO: 19) | TNFα |
| KSPCQRETPEGAEAKPW | (SEQ ID NO: 20) | |

These peptides are covalently bound to a carrier (KLH) according to a standard recipe. The conjugate dissolved in PBS is mixed in equal shares with Freund's adjuvant. The individual inoculation dose is set in such a way that it contains 200 pg of the peptide belonging to the antigen in question. 15-week-old young hens are im-

EXAMPLE 2

Production of Polyclonal Antibodies by Means of Lipopolysaccharides (LPS)

Cleaned LPS (SIGMA) of *E. coli* J5 are dissolved in PBS and mixed in equal shares with Fueund's adjuvant. 15-week-old young hens are immunised with this mixture. The LPS dose amounts to 1 mg of LPS per immunisation. Boostering is done 4 times at intervals of 4 weeks.

EXAMPLE 3

Obtaining the Antibodies (IgY) from Egg-Yolk:

The eggs from the clutches of the immunised hens are collected. After separation of the egg-yolk containing antibodies, there is storage at −20° C. According to requirements, the yolks are thawed and treated according to the following plan (C. SCHWARZKOPF, B. THIELE (1996) ALTEX 13 Suppl. 16, 35–3):

A TBS: 20 mM Tris/HCl, pH 7.5, 0.5 M NaCl

B 10% (w/v) dextra sulphate in A Solutions

C 1 M $CaCl_2$

D 0.5 M EDTA, pH 7.5

E saturated ammonium sulphate solution

The egg yolk (corresponds to a volume of 10–20 ml/egg-yolk) is suspended in 100 ml TBS per egg-yolk. Lipids and lipoproteins are precipitated with dextran sulphate (6 ml B per 100 ml TBS/egg yolk suspension) and $Ca^{++}$ (15 ml C per 100 ml TBS-egg yolk suspension), stirred for 30 to 60 min. at room temperature and centrifuged off at 5,000 g. The pellet is washed with a small volume of TBS (approx. 20 mlg/egg yolk) and centrifuged again.

The combined supernatants are filtered through a paper filter, then 0.5 M EDTA is added to the filtrate up to a final concentration of approx. 30 mM EDTA (6 ml per 100 ml), in order to bind remaining $Ca^{++}$ ions. After this, the supernatant is mixed with 24.3 g of ammonium sulphate per 100 ml (corresponds to 40% saturation) and incubated at +4° C. for 30 min.. The resultant precipitation (IgY) is firstly washed with 30% $(NH_4)_2SO_4$ (30 ml E+70 ml dist. water), centrifuged, then dissolved in the smallest possible volume of TBS (approx. 10 ml/egg-yolk used) and dialysed against TBS.

The content of IgY is determined photometrically at 275 nm.

EXAMPLE 4 a) Activation of a Carrier:

The IgY cleaned according to Example 3 are covalently bound to a suitable carrier. For example, sepharose can be activated as described below for this purpose (H.- F. Boeden, W. Büttner, C. Rupprich, B. Büttner, S. Heinrich, M. Becker, M. Holtzhauer (1992) Makromol. Chem. 193, 865–887):

The agarose carrier is gradually transformed, i.e. with an amount of acetone increasing in steps of 20%. Finally, the carrier is left to stand in an enclosed container in a quintuple bed volume with water-free acetone overnight, again washed with 5 to 10 Vol. water-free acetone and briefly sucked off on a G2 slice. 400 mg N-(Chlorcarbonyloxy)-5-norbornen-2,3-dicarboximid (CICOONB) in 10 ml water-free acetone p.a. are added to 10 ml sedimented carrier. Within 15 minutes, a solution of 280 μl triethylamine and 20 mg 4-dimethylamino-pyridine (DMAP) in 5 ml dry acetone is added drop by drop (mol ratio CICOONB:triethylamine:DMAP 1:1.2:0.1) with shaking. After this, there is further shaking for 15 minutes, after which the carrier is washed with about 200 ml water-free acetone.

b) Coupling of the IgY to a Solid Carrier:

The polysaccharide matrix (gel) activated according to Example 4a) is gradually transformed into a watery medium and then immediately stirred into the coupling solution containing the ligand. Citrate buffer pH 4.2 is used as a coupling buffer. The coupling is done with gentle shaking for 2 h at room temperature. Free bindings are subsequently blocked by addition of ethanolamine. Table 2 shows the concrete conditions for the individual antibodies.

TABLE 2

| Gel No. | Chicken-Ab (lgY) | mg | mg/ml | Ab solution (ml) | ml coupling buffer (Citrate, 0.1 M, pH 4.2) | Ethanol-amine 1 M (ml) | moist gel (g) |
|---|---|---|---|---|---|---|---|
| 1 | ChaIL1 | 9.5 | 13.5 | 0.7 | 4.3 | 0.5 | 5.55 |
| 2 | ChaIL6 | 9.8 | 9.8 | 1.0 | 4.0 | 0.5 | 5.58 |
| 3 | ChaIL10 | 9.2 | 7.4 | 1.2 | 3.8 | 0.5 | 5.55 |
| 4 | ChaTNF | 11.0 | 11.6 | 1.0 | 4.1 | 0.5 | 5.56 |
| 5 | ChaLPS | 11.6 | 13.7 | 0.9 | 4.2 | 0.5 | 5.60 |
| 6 | ChaC3a | 6.9 | 10.7 | 0.6 | 4.4 | 0.5 | 5.57 |
| 7 | ChaC5a | 11.3 | 11.1 | 1.0 | 4.0 | 0.5 | 5.55 |
| 8 | Control | 0.0 | 0.0 | 0.0 | 5.0 | 0.5 | 5.61 |

EXAMPLE 5

The antibodies immobilised according to Example 4 are used in order to remove lipopolysaccharides, interleukins, TNF or complement factors from liquid media such as buffer solutions, serum or blood plasma.

For this, the carriers are washed, transformed into a physiological buffer (PBS) and packed in plastic or glass pillars free of air bubbles. The arrangement is completed by connection to a chromatography appliance. The sample material to be adsorbed (buffer doted with the antigens, serum or blood plasma samples, doted or with natural antigen content) can now be guided by gravity or with a suitable pump via the immobilised antibodies specific for the antigens stated. The existing antigens are recognised, firmly bound and thus removed from the medium flowing through the column by the IgY. The detection of the effectivity is done by analysis (ELISA) of the column throughflow, the antigen content of which is reduced. After washing of the column with a physiological buffer, there is desorption of the bound antigen with suitable elution agents (0.1 M citrate buffer pH 3), fractioning and analysis of the eluate. Quantitative detection of the antigens is used to determine the capacity of the immunosorbent.

What is claimed is:

1. An immunoadsorber for blood treatment use in sepsis therapy, the immunoadsorber comprising a carrier of organic or synthetic polymers to which are immobilized antibodies that are specific to C3a and/or C5a and to lipopolysaccharides (LPS) and wherein,
   a) the antibodies to C3a are specific for at least one peptide selected from the group consisting of SEQ ID NO: 1, 2, and 3; and
   b) the antibodies to C5a are specific for at least one peptide selected from the group consisting of SEQ ID NO: 4, and 5.

2. The immunoadsorber according to claim 1, wherein the antibodies are polyclonal antibodies.

3. The immunoadsorber according to claim 2, wherein the antibodies are avian antibodies of type IgY.

4. The immunoadsorber according to claim 1, further comprising at least one immobilized antibody specific for at least one sepsis mediator selected from the group consisting of TNF, 1L1, 1L6 , IL8 and/or IL10.

5. The immunoadsorber of claim 4, wherein the immobilized antibodies comprising the immunoadsorber are varied as a function of the actual content of sepsis mediators in the blood.

6. The immunoadsorber according to claim 4, wherein the immobilized antibodies are specific for at least one of the following peptide sequences of interleukins 1α and 1β

IL1α: NH2-NCYSENEEDSSSID-COOH SEQ ID NO. 6
NH2-GAYKSSKDDAKIT-COOH SEQ ID NO. 7
NH2-WETHGTKNYFTS-COOH SEQ ID NO. 8
ILβ: NH2-RISDHHYSKGFRQA-COOH SEQ ID NO. 9
NH2-VQGEESNDKIPVA-COOH SEQ ID NO. 10
NH2-ESVDPKNYPKKKMEKRF-COOH SEQ ID NO. 11.

7. The immunoadsorber according to claim 4, wherein the immobilized antibodies are specific for at least one of the following peptide sequences of interleukin 6:

IL6: NH2-APHRQPLTSSERIDKQI-COOH SEQ ID NO. 12
NH2-QNRFESSEEQARA-COOH SEQ ID NO. 13
NH2-AITTPDPTTNAS-COOH SEQ ID NO. 14.

8. The immunoadsorber according to claim 4, wherein the immobilized antibodies are specific for at least one of the following peptide sequences of interleukin 10

IL10: NH2-SPGQGTQSENSCT-COOH SEQ ID NO. 15
NH2-QMKDQLDNLLLKES-COOH SEQ ID NO. 16
NH2-MPQAENQDPDIKA-COOH SEQ ID NO. 17
NH2-LPCENKSKAVEQ-COOH SEQ ID NO. 18.

9. The immunoadsorber according to claim 4, wherein the immobilized antibodies are specific for at least one of the following peptide sequences of TNFα

TNFα: NH2-VRSSSRTPSDKPVA-COOH SEQ ID NO. 19
NH2-KSPCQRETPEGAEAKPW-COOH SEQ ID NO. 20.

10. The immunoadsorber according to claim 1, wherein the organic or synthetic polymers further comprise membranes or particles of one or more of the group consisting of polystyrenes, carbohydrates, cellulose, agarose derivatives, and acrylates.

11. The immunoadsorber according to claim 1, wherein the immobilized antibodies are covalently bound to the carrier.

12. The immunoadsorber according to claim 1, wherein the immobilized antibodies are attached to the carrier via spacers or linkers.

13. A method for the production of immunoadsorber according to claim 1, wherein antibodies specific for C3a and/or C5a and LPS and, optionally, against further sepsis mediators are covalently or adsorptively coupled to the carrier.

14. A method according to claim 13, wherein the antibodies are produced by immunisation of mammals or birds with the corresponding antigens.

15. The method of claim 14 wherein the antibodies are raised by immunizing one or more animals selected from the group consisting of mice, rats, rabbits or chickens.

16. A method of treating blood plasma or serum using the immunoadsorber of claim 1, the method comprising the steps of, providing an amount of blood plasma or serum in need of sepsis therapy; and contacting the blood with the immunoadsorber of claim 1;

and recovering the contacted blood plasma or serum from the immunoadsorber.

17. The method of claim 16, wherein the blood plasma or serum has not been subjected to hemofiltration prior to contacting the immunoadsorber.

* * * * *